United States Patent
Kohl et al.

(10) Patent No.: US 12,215,304 B2
(45) Date of Patent: Feb. 4, 2025

(54) INTEGRATED ETHANOL AND PRETREATMENT FACILITY

(71) Applicant: CHEMTOR, LP, Lockhart, TX (US)

(72) Inventors: Scott D. Kohl, Maize, KS (US); Rana K. Mohamed, Austin, TX (US); Wade Gossett, Buda, TX (US)

(73) Assignee: CHEMTOR, LP, Lockhart, TX (US)

( * ) Notice: Subject to any disclaimer, the term of this patent is extended or adjusted under 35 U.S.C. 154(b) by 0 days.

(21) Appl. No.: 18/305,805

(22) Filed: Apr. 24, 2023

(65) Prior Publication Data
US 2023/0357678 A1    Nov. 9, 2023

Related U.S. Application Data

(63) Continuation of application No. PCT/US2021/071962, filed on Oct. 21, 2021.
(Continued)

(51) Int. Cl.
| | | |
|---|---|---|
| C12F 3/06 | (2006.01) | |
| C07C 29/74 | (2006.01) | |
(Continued)

(52) U.S. Cl.
CPC .................. *C12F 3/06* (2013.01); *C10G 3/60* (2013.01); *C10G 2300/1014* (2013.01); *C10G 2300/1055* (2013.01); *C10G 2400/04* (2013.01)

(58) Field of Classification Search
CPC ....... A61M 5/002; A61M 5/008; Y02E 10/50; Y02E 50/10; C07C 29/74; C07C 31/08;
(Continued)

(56) References Cited

U.S. PATENT DOCUMENTS

| | | |
|---|---|---|
| 3,754,377 A | 8/1973 | Clonts |
| 3,758,404 A | 9/1973 | Clonts |
(Continued)

FOREIGN PATENT DOCUMENTS

| | | |
|---|---|---|
| WO | WO 2019/213290 A1 | 11/2019 |
| WO | WO 2020/198595 A1 | 10/2020 |

OTHER PUBLICATIONS

International Search Report and Written Opinion issued by the United States Patent and Trademark Office as International Searching Authority for PCT/US2021/071962, dated Feb. 28, 2022, 10 pages.
(Continued)

*Primary Examiner* — Ellen M McAvoy
*Assistant Examiner* — Chantel Graham
(74) *Attorney, Agent, or Firm* — Haynes and Boone, LLP; Michael J. Tobin; Clint Wilkins

(57) ABSTRACT

An integrated facility for the co-production of ethanol and the pretreatment of impure vegetable oils, waxes and (animal) fats is provided. A by-product from the ethanol plant, such as distillers corn oil or distillers sorghum oil, can be directly refined on site to remove contaminants such as metals, phospholipids and inorganic anions, to enable use as ready feedstocks for a renewable diesel hydrotreatment plant. The utility of the ethanol plant infrastructure can be directly harnessed to pretreat and purify a variety of impure feedstock materials. The pretreatment reduces catalytic poisoning in the reduction process at refining facilities during the synthesis of renewable diesel. By-products of the pretreatment process are recycled to various parts of the ethanol plant for incorporation into the animal feed(s) produced by the ethanol plant or incorporated into the existing wastewater treatment and disposal system within the ethanol plant.

18 Claims, 2 Drawing Sheets

Related U.S. Application Data

(60) Provisional application No. 63/104,354, filed on Oct. 22, 2020.

(51) Int. Cl.
*C07C 31/08* (2006.01)
*C10G 3/00* (2006.01)

(58) Field of Classification Search
CPC .... C10G 2300/1014; C10G 2300/1055; C10G 2400/04; C10G 3/60; C12F 3/06
See application file for complete search history.

(56) References Cited

U.S. PATENT DOCUMENTS

| | | | |
|---|---|---|---|
| 3,992,156 | A | 11/1976 | Clonts |
| 4,491,565 | A | 1/1985 | Verachtert |
| 7,618,544 | B2 | 11/2009 | Massingill, Jr. |
| 8,128,825 | B2 | 3/2012 | Massingill |
| 8,722,924 | B1 | 5/2014 | Overheul et al. |
| 9,815,001 | B2 | 11/2017 | Massingill |
| 2015/0041305 | A1 | 2/2015 | Overheul et al. |
| 2015/0125913 | A1* | 5/2015 | Overheul ............... C10L 1/02 435/294.1 |
| 2015/0152372 | A1 | 6/2015 | Kohl et al. |
| 2017/0014733 | A1 | 1/2017 | Massingill |
| 2017/0298393 | A1 | 10/2017 | Barr et al. |
| 2019/0211291 | A1 | 7/2019 | Svetlichny et al. |
| 2021/0069667 | A1 | 3/2021 | Davis et al. |

OTHER PUBLICATIONS

International Preliminary Report on Patentability issued by The International Bureau of WIPO on behalf of the International Searching Authority for International Application No. PCT/US2021/071962, issued Apr. 13, 2023, 7 pages.

\* cited by examiner

INTEGRATED ETHANOL AND PRETREATMENT FACILITY

CROSS-REFERENCE TO RELATED APPLICATIONS

This application is a continuation of PCT International Patent Application No. PCT/US2021/071962 filed Oct. 21, 2021, titled "INTEGRATED ETHANOL AND PRETREATMENT FACILITY," which claims benefit of U.S. Provisional Patent Application No. 63/104,354 filed Oct. 22, 2020, titled "INTEGRATED ETHANOL AND PRETREATMENT FACILITY," which are incorporated herein by reference in their entirety.

FIELD OF THE DISCLOSURE

The present disclosure generally pertains to an integrated facility for the co-production of ethanol and pretreated feedstocks for renewable fuel. In particular, the present disclosure relates to an integrated facility and associated extraction process for refining oils and waxes isolated from the whole stillage, thin stillage, and/or syrup of a grain ethanol distillation process.

BACKGROUND

Vegetable oil is a by-product of grain ethanol production. The oil is generally carried through the fermentation and distillation portions of an ethanol plant into the whole stillage that is removed from the distillation system. The whole stillage is commonly separated into a thin stillage, which includes the vegetable oil, and a cake that can be dried to produce dried distillers grains with solubles (DDGS), which can be used as an animal feed. The thin stillage can be processed to remove moisture therefrom and form nutritive syrup that can also be used as an animal feed material. Additionally, during the evaporative concentration, a fraction of the vegetable oil may be extracted from the concentrated thin stillage and be made a saleable product. The vegetable oil extracted from the concentrated thin stillage has many industrial uses, such as in animal feed ingredient, soaps, paints, rustproofing materials, inks, textiles, and insecticides. The vegetable oil can also be used as a feedstock in the production of alternative fuels such as biodiesel and renewable diesel.

Renewable diesel generally refers to diesel fuel consisting of long chain hydrocarbons derived from the hydrogenation of vegetable oils (including waste oils) and/or animal oils (i.e., animal fat) ("feedstock oil"). One method of producing renewable diesel is by reduction of a feedstock oil. Hydrotreatment of lipid rich feedstocks, such as vegetable oils and animal fats is a widely utilized and reliable process in the production of renewable diesel around the world. Unlike Biodiesel, which is generally not considered to be a full replacement of conventional petrodiesel for use in most diesel engines, renewable diesel is structurally similar to petrodiesel as it is primarily composed of hydrocarbon chains and thus can be used directly into diesel engines without modifications. This removes the restriction of blending requirements with petrodiesel and facilitates use in the retail diesel fuel marketplace.

Several reaction schemes exist for conversion of vegetable oil (and other low-cost feedstocks) into renewable diesel. Hydrotreating is one such process in which the vegetable oil feedstock is reacted with hydrogen under elevated temperature and pressure to change the chemical composition of the feedstock. In the case of renewable diesel, hydrogen is introduced to the feedstock in the presence of a catalyst which converts the triglyceride molecules into paraffinic hydrocarbons. In addition to creating a fuel that is very similar to petrodiesel, this process creates other hydrocarbon byproducts including lower hydrocarbon fuel gas compounds (e.g., methane, ethane, propane, and butane) and higher hydrocarbon naphtha.

Low-cost renewable diesel feedstocks often contain contaminants that must be removed collectively prior to upgrading by conventional refinery processes into clean hydrocarbon fuels or chemicals. The purification processes for removing contaminants, thereby raising the economic value of these low-cost feedstocks, generally utilize solvent extractions, filtration, or distillation methods as the refining strategy. Such energy intensive processes would necessitate additional infrastructure to process the waste streams generated as well as mapping out of transport of these feedstocks through railway tankers, tanker trucks and surface water vessels.

Vegetable oils from sources, such as, for example used cooking oil (UCO) or crude soybean oil, are often pre-aggregated. Vegetable oils derived from an ethanol facility are produced at plant locations remote from the renewable diesel facility. Transport of these materials to a pretreatment facility incurs substantial cost and logistic demand. The infrastructure and transportation cost increases the overall expense in the manufacture of renewable diesel and decreases its competitiveness with petrodiesel as an alternative fuel source.

DETAILED DESCRIPTION

Figure 1:
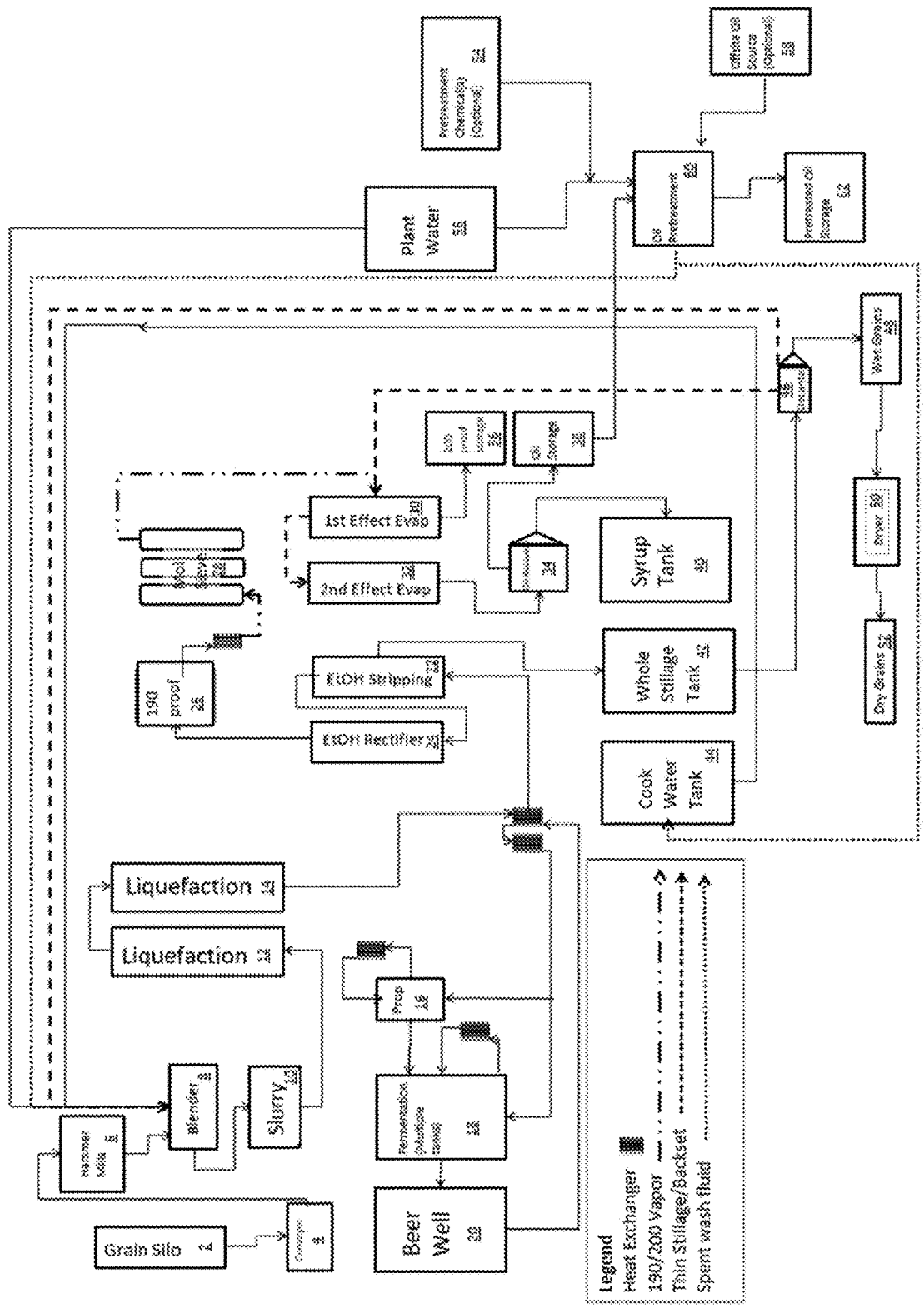
FIG. 1 is a schematic diagram of an integrated ethanol and renewable diesel pretreatment facility in accordance with an embodiment of the present disclosure.

The present disclosure overcomes many of the problems outlined above and provides improved processes and plant systems for the co-production of ethanol and purified feedstocks for the renewable fuel in combined facilities having both an ethanol plant and a pretreatment plant, wherein the plants are located in close proximity allowing various products, reagents, utilities, and by-products from each plant to be easily transferred to the other plant as desired to increase the efficiency of the overall, dual-plant facility. More specifically, this co-integration facilitates the processing of the wastewater stream as a minor, negligent percentage of the total water processed through an ethanol facility.

According to one or more embodiments of the present disclosure, oils and waxes isolated from the whole stillage, thin stillage, and/or syrup of a grain ethanol distillation process are refined in an extraction process which consistently removes 70-95% of impurities such as inorganic salts, transition metals, chlorides, sediment, and phospholipids present that would otherwise poison the catalytic activity of hydrotreatment catalysts used in the reduction process to transform the material into renewable diesel. The pretreatment process is designed to operate within the same general facility as the corn ethanol plant to capitalize on the infrastructure present and the facile capacity to handle aqueous effluent. Namely, the oil can be pretreated at the ethanol fermentation facility using wash waters already present. The refinement process can be tailored to a variety of feedstocks including distillers corn oil (DCO), UCO, animal fats and is designed in such a way that the waste streams produced during oil pretreatment are easily managed through the recycling and animal feed production capacity present in the ethanol plant. Vegetable oils from other sources that have undesired impurities, such as, crude soybean oil, crude canola oil, crude peanut oil, crude corn oil, yellow grease, brown grease, tallows and similar oils can also be directly refined on site to remove contaminants such as metals, phospholipids and inorganic anions, to enable use as ready feedstocks for a renewable diesel hydrotreatment plant. The spent wastewater from the pretreatment process can be readily handled within the existing water handling system of the ethanol plant. This synergy effectively eliminates the cost of procuring pretreatment wash fluids and, more importantly, eliminates the disposal of the spent wash fluids from the pretreatment process, as discussed in further detail below.

At a typical corn-based ethanol plant, pretreatment of the oil byproduct recovered from the stillage processing system produces a modest amount of spent wash fluid. Treatment of this on-site generated crude oil results in a spent wash fluid that is generally less than 5% of the water recycling capacity of the facility for the creation of animal feeds. Impure oils from other ethanol plants or other sources can be pretreated at the ethanol plant and the spent wash fluid returned to the ethanol plant for recycling and the creation of animal feeds.

In one aspect of the disclosure, an integrated process for the co-production of ethanol and purified renewable diesel feedstock comprises the steps of fermenting carbohydrate rich solutions to ethanol, distilling an ethanol-containing beer within distillation apparatus of an ethanol plant using oil and carbohydrate containing raw materials as a feedstock and producing ethanol and a vegetable oil product. Thereafter, the vegetable oil product is directed from the ethanol plant to a proximal pretreatment plant; the vegetable oil product and an aqueous based extractant solution are used in a liquid-liquid extraction process in the pretreatment plant, where the vegetable oil product and aqueous extractant solution are contacted and then separated to yield the purified vegetable oil in which a substantial amount of catalyst poisons are removed including metal, phospholipid, sediment, and inorganic anions, such as chloride. The resultant waste stream comprising an aqueous extractant solution comprising water soluble as well as, in some cases, precipitated impurities or solid particles can be transferred back to the ethanol plant for recycling and use therein.

In one or more embodiments, the oil purification/pretreatment process uses low shear pumps when moving the oil into and out of the purification device, such as positive displacement pumps, to minimize the creation of emulsions. In one or more embodiments, the oil purification/pretreatment process uses a high surface area contactor device that produces intimate contact between the water phase and oil phase to facilitate rapid mass transfer of water-soluble components from the oil into the water. In one or more embodiments, the high surface area contactor device produces adequate mass transfer without creating turbulent flow thereby minimizing any production of emulsions.

In one or more embodiments, the high surface area contactor device can be a fiber packed conduit reactor, such as described in U.S. Pat. Nos. 3,754,377; 3,758,404; 3,992,156; 4,491,565; 7,618,544; 8,128,825; and/or 9,815,001, and/or U.S. Patent Application Publication No. 2021/0069667, which are hereby incorporated by reference in their entireties.

In one or more embodiments, the purified lipid rich feedstock contains a residual amount of water that must be removed prior to use in the hydrogenation step required to convert triglycerides, diglylcerides, monoglycerides, free fatty acids, and fatty alcohols into renewable diesel. In one or more embodiments, the water can be removed through a settling tank or decanter tank allowing the higher density water to gravity settle out of the bulk oil phase. After gravity settling, the top layer in the settling tank has substantially lower water content. In one or more embodiments, the water can be removed through artificial gravity creation through any suitable device including, for example: centrifuge, disk centrifuge, hydrocyclone, whirlpool separator, or solid bowl decanter. In one or more embodiments, the water can be removed through filtration and/or absorption into hydrophilic sorbent. In other embodiments, the water can be removed with a thermal evaporation drying step, dependent on the feedstock of choice, could be readily incorporated or combined with a process steam overhead generated by an existing evaporation system used to recover the vegetable oil by-product at the ethanol plant. Other suitable water removal techniques are known to those of ordinary skill in the art. The energy source for the water removal can be obtained from the substantial utility source present at the ethanol facility reducing the capital for heat generation equipment.

In another aspect of the disclosure, the wastewater generated as a by-product in the purification of crude vegetable oil in the pretreatment plant is directed back to the ethanol mixture with the beer, and/or may be added to a concentrated thin stillage product, which is further processed to generate a mineral rich or phospholipid rich syrup.

In another aspect of the disclosure, the wastewater generated as a by-product in the purification of crude vegetable oil in the pretreatment plant is directed back to the grain slurry process of the ethanol plant. The aqueous waste of the oil purification process becomes part of the mash bill allowing ions and other materials contained therein to be utilized by the fermentation process.

A still further aspect of the disclosure involves use of the bottoms of the aqueous waste stream, principally comprising high boiling components, minerals, and phospholipids can be added to the Solids output from the ethanol plant (e.g., a cake), which are normally used to produce animal feeds.

In another aspect of the disclosure, vegetable oils, fats and waxes needing pretreatment for renewable diesel production sourced from outside the ethanol production plant product streams can be treated at the ethanol plant site. The wastewater generated as a by-product in the purification of these materials in the pretreatment plant is directed back to the ethanol plant in any of the locations previously described.

The disclosure also provides integrated plants for the coproduction of ethanol and renewable diesel pretreatment facility for low-cost inputs corresponding to the foregoing method aspects of the disclosure. Thus, such a facility may include an ethanol plant comprising apparatus operable to produce ethanol and a vegetable oil product from an ethanol-containing beer; and a pretreatment plant comprising a reactor assembly operably coupled with the ethanol plant apparatus to receive at least one of the following: some, up to all, of the vegetable oil product from the ethanol plant and/or vegetable oils, fats and/or waxes needing pretreatment for renewable diesel production sourced from outside the ethanol production plant product streams, and to react these crude vegetable oils, fats and/or waxes product with the aqueous extractant solution to produce purified vegetable oils, fats and/or waxes and outputs such as the mineral and phospholipid enriched aqueous liquid by-product containing water; inorganic and organic salts in the form of phospholipids; and/or the sediment-rich bottoms from the wash water. Transfer structure(s), typically standard interconnecting transfer pipes or lines, are provided to direct one or more of the outputs from the pretreatment plant as desired to the ethanol plant for use therein, in some or all of the ethanol plant locations described previously. It will be appreciated that the present disclosure maximizes the efficiencies of both the ethanol and pretreatment plants forming a part of the overall production facilities contemplated by the disclosure. Thus, the principal byproducts of the ethanol plant, namely vegetable oil, need not be transported great distances thereby giving significant savings. Nor is there a need to build novel infrastructure to manage the newly generated waste-water stream that is produced in the process.

Turning now to FIG. 1, an integrated ethanol and pretreatment facility is illustrated including several optional features, such as using existing ethanol plant water streams with optional chemical addition for the pretreatment of vegetable oil derived from the ethanol plant operation and/or oils derived from offsite production. Spent wash waters from the pretreatment of the renewable diesel feedstock can be returned to a number of locations within the ethanol production facility with common locations being directed as part of the mash bill or as "cook waters" for use in various parts of the plant operation.

The facility broadly comprises an ethanol plant and a pretreatment plant. As illustrated, the ethanol plant and pretreatment plant are co-located so that products and by-products, utilities, infrastructure, and labor pool of each facility can be readily shared, thereby reducing equipment and operating costs for the overall facility. As used herein, the term "by-product" refers not only to mineral phospholipid rich waste stream, but materials fed to a crude oil/feedstock pretreatment vessel that are later recovered from the pretreatment vessel and separated into purified oil (renewable diesel feedstock) and aqueous waste stream. The ethanol plant may be configured in a conventional manner, with the starting biomass material undergoing initial processing and fermentation to produce an ethanol-containing "beer." In the embodiment illustrated, the ethanol plant utilizes a biomass material as the source of carbohydrates and sugars for the fermentation process. A plant or vegetable oil is an important by-product of the ethanol plant, in as much as this by-product forms the crude input to the pretreatment plant, so that the biomass material should contain suitable amounts of plant oils. Exemplary biomass feed materials include corn, sorghum, wheat, barley and pearl millet. In the U.S., corn is the predominant feedstock for fuel ethanol production. Accordingly, the description set forth below is made with respect to corn and corn by-products. However, it should be understood that this description is exemplary only and should not be taken as a limitation on the scope of the present disclosure.

The preparation and fermentation of corn feedstock within the ethanol plant may be carried out according to any number of methods known to those skilled in the art, and thus need not be fully described herein. In any case, following fermentation, the resultant ethanol-containing beer may be stored within a beer well 20 while it awaits further processing. Typically, the beer comprises from about 10-24% by volume ethanol, or about 16% by volume ethanol. The beer also contains from about 5-20% by weight solids, or about 12% by weight solids. Solids as used herein are defined as materials other than ethanol and water (which may include, e.g., dissolved solids, liquids, or dissolved gases). The beer is fed to distillation apparatus for separation and recovery of the ethanol contained therein. Distillation apparatus, which may comprise one or more distillation columns 22, 24, produces an overhead stream ("190/200 Vapor" in FIG. 1) primarily comprising ethanol and some water (e.g., from about 80-99% by volume ethanol, or from about 90-98% by volume ethanol, or about 95% by volume ethanol), with the balance of the stream primarily including water. To be suitable for use as fuel-grade ethanol, the remaining water needs to be removed from the overhead stream. This water separation may be accomplished by means of a dehydration unit (mol sieves) 28, which can be equipped with molecular sieve technology to achieve this separation. In certain embodiments, the molecular sieve comprises an alumino silicate material. In certain embodiments, stream is condensed so that a portion can be refluxed back to the incorporated apparatus, however, this need not always be the case. In those embodiments in which overhead stream was previously condensed, the stream should be vaporized before it is passed to the dehydration unit. This vaporization can be accomplished by one or more heat exchangers fed with steam supplied via a plant distribution header. A substantially pure ethanol stream (i.e., greater than 99% by volume ethanol, or approximately 200 proof) exits the dehydration unit 28 and is stored in a storage vessel 36 to await further processing.

As illustrated in FIG. 1, one of the feedstock inputs 54, 56, 58 to the pretreatment plant contains an aqueous extractant solution. The solvent in this process can be directly acquired from the pre-existing infrastructure in which water is purified and recycled, either alone or mixed with the extractant of choice. Thus, the aqueous containing input to pretreatment vessel 60 is either pure water, chelating solution or other chemically useful solution for impurity reduction. The bottoms from the distillation apparatus 22, 32 comprise a whole stillage stream that is directed to tank 42 and oil recovery apparatus 34, respectively. Several products can be produced from whole stillage stream including corn oil (oil storage 38), a nutritive corn syrup (syrup tank 40), and mineral enriched, phospholipid enriched dried distillers grains with solubles (DDGS) 52. The whole stillage stream from tank 42 may be separated by a centrifuge into a thin stillage stream and a cake stream. The thin stillage stream generally comprises between about 5% to about 10% by weight solids or about 7% by weight solids. The balance of the thin stillage comprises mainly water and corn oil. The thin stillage is concentrated within a multiple-effect evaporator 30, 32. Steam from the steam distribution header is introduced into a first effect 30 in indirect heat exchange relationship with the thin stillage stream. Moisture is evaporated from the thin stillage and removed from the first effect 30 as process steam stream. The concentrated stillage product is removed from first effect 30 via line and a portion of the corn oil contained therein is separated. The separation of the corn oil may be achieved through the use of a mechanical separation device, such as a decanter system or a disc stack unit 46. The concentrated stillage product (minus the corn oil that was removed) may be passed through indirect heat exchange, which causes a portion of the moisture contained within the concentrated stillage product to evaporate. This vapor is returned to the distillation apparatus.

The stillage product now comprises a viscous syrup from which corn oil is recovered by means of a secondary separation device and stored (oil storage 38) to be directed to the pretreatment plant as a feedstock input thereto. In an alternate embodiment of the present disclosure, the corn oil may be extracted prior to fermentation. For example, the corn oil may be extracted via pressing or solvent extraction prior to fermentation. In such case, the processing of the thin stillage occurs as mentioned above, with the exception of corn oil recovery. The cake stream from centrifuge may be conveyed toward drying apparatus 50 in which moisture is removed and DDGS produced. As previously described, there are two feedstock inputs to the oil pretreatment vessel, namely an aqueous extractant solution including water from plant water 56 (some embodiments may also include other pretreatment chemicals 54) and a corn oil stream from oil storage 38. These feedstocks are directed to extraction reactor system (pretreatment vessel 60) where the corn oil undergoes a first extractant wash. Depending on the purity and specification limits desired in the final purified corn oil output, the washed oil maybe be subjected to a second extraction wash or more than two extraction washes in which additional extractant solution is used. The purified product may then be stored in the pretreated oil storage tank 62 or piped to a dryer to remove any residual water and stored in wash/dry tank (not shown).

FIG. 1 additionally illustrates a still further embodiment of the disclosure, wherein the spent wash fluid is integrated back into the plant. In a conventional pretreatment/refining plants, the wastewater generated alone must undergo treatment before being disposed of or recycled. This requires additional separation equipment, which represents a significant capital expense, and moreover the separation requires an energy input. In the present disclosure, however, use is made of the existing separation equipment present in the ethanol plant to further process aqueous mixtures, namely distillation, evaporation, centrifugation and drying. As such, capital equipment costs are reduced, and very little additional energy is required.

It is understood that the various integrations between pretreatment plant and ethanol plant described above may be carried out jointly, individually, or in any combination thereof, as the requirements of any given facility dictate. However, use of the aqueous and corn oil outputs from the ethanol plant, coupled with the use of the pretreatment plant waste stream, is believed to the give significant efficiency advantages.

Figure 2:
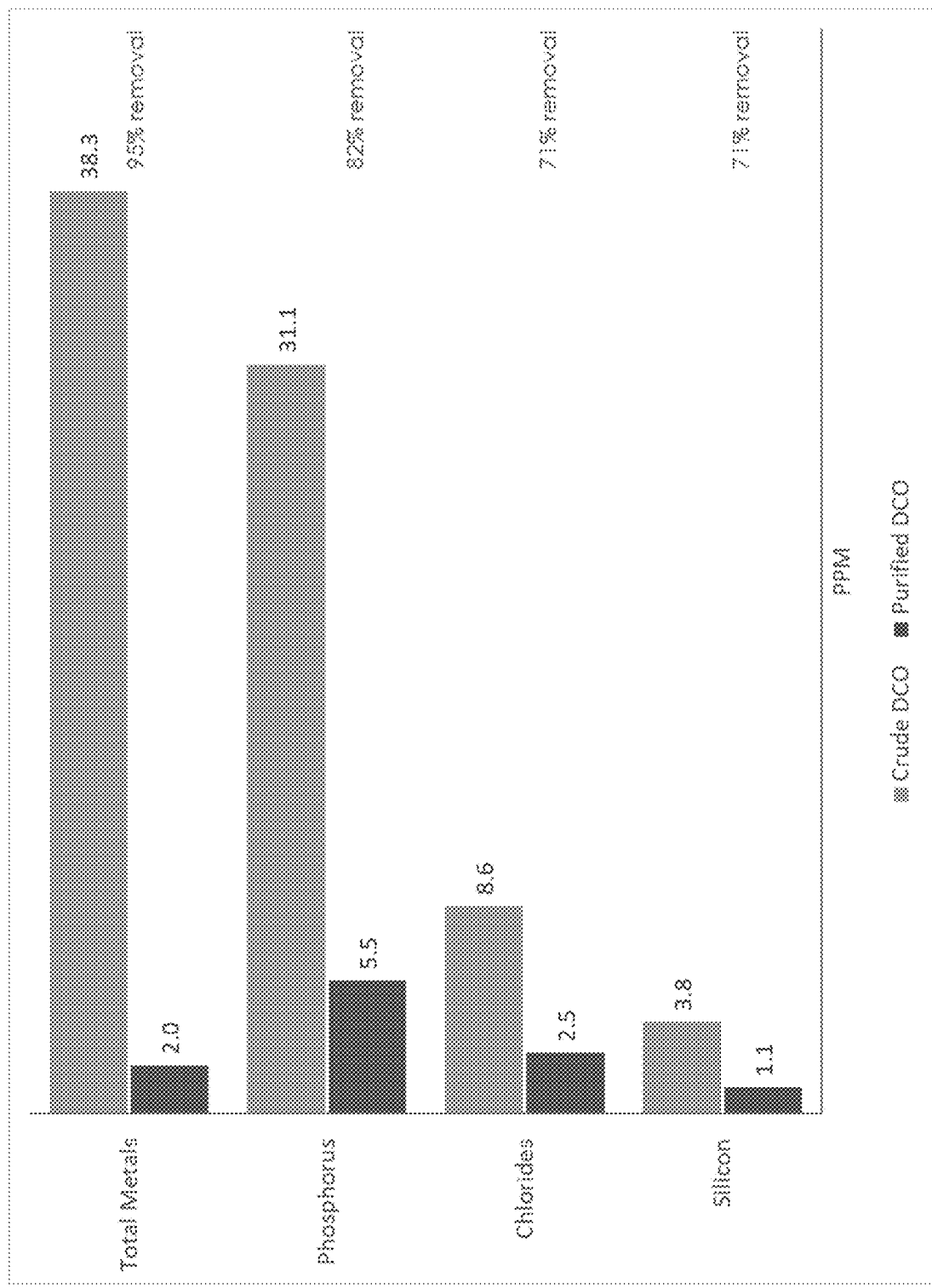
FIG. 2 is a chart demonstrating extraction efficiencies achieved in the purification of crude DCO.

Turning now to FIG. 2. which illustrates the extraction efficiencies which can be achieved in a pretreatment process in which crude DCO, in an embodiment example, acquired from an ethanol plant is purified using an optimized process which effectively 95% of total metals, 82% of phosphorus, 71% of chlorides, and 71% of silicon impurities to bring the total impurity level from 73.2 ppm to 8.6 ppm, well below the 24 ppm specification limit required for the majority of feedstocks utilized in the hydrotreatment process to synthesize renewable diesel. In the purification process, the phosphorus level was reduced by 82% from 31.1 ppm to 5.6 ppm, effectively degumming the oil below the phosphorus specification limit of 10 ppm, which is required to attenuate the poisoning (aka "sugaring") of hydrotreatment catalysts.

According to one or more embodiments, the integrated ethanol and pretreatment facility comprises an integrated ethanol and biodiesel facility. An example of an integrated ethanol and biodiesel facility is disclosed in U.S. Pat. No. 8,722,924 B1, which is hereby incorporated in its entirety.

EXAMPLES

Example 1

Extraction efficiency was measured for a single wash stage using a fiber reactor contactor device (see U.S. Pat. No. 7,618,544, which is hereby incorporated in its entirety) with water as the sole extracting chemical in which crude DCO was the oil being pretreated. In these examples, DCO acquired from an ethanol plant is purified using single wash step or single washing pass with water as the only washing ingredient. The average chloride removal achieved was 72%. The average metal ion removal rates was 79%. The average phosphorous removal rate was 87%. The results are summarized in Tables 1A, 1B, and 1C below.

TABLE 1A

| Analysis/ Method | | | End user maximum allowed | Aggregate crude oil | Example 1 | Example 2 | Example 3 |
| --- | --- | --- | --- | --- | --- | --- | --- |
| D2709 | Total S&W | vol. % | | 2.4 | <0.010 | <0.010 | <0.010 |
| D7536, Chloride In Hydrocarbons By XRF | Total Chloride | mg/kg | 5 | 10.78 | 3.02 | 2.81 | 2.97 |
| | | | | CL Removal: | 71.99% | 73.93% | 72.45% |
| Free Fatty Acids | Free Fatty Acids (calc) | % | 15 | 12.4 | 12.4 | 12.5 | 12.4 |
| D5708M (Calcium) | Calcium | ppm (wt.) | | 0 | 1.2 | 0.9 | 0.9 |
| D5708M (Magnesium) | Magnesium | ppm (wt.) | | 1.1 | 0.1 | 0.1 | 0.1 |
| D5708M (Sodium) | Sodium | ppm (wt.) | | 1.5 | 0 | 0 | 0.2 |
| D5708M (Potassium) | Potassium | ppm (wt.) | | 12 | 0.4 | 0.1 | 0.1 |
| D5708M (Phosphorous) | Phosphorus | ppm (wt.) | 10 | 10.6 | 1.2 | 1.1 | 1 |
| D5708M (Nickel) | Nickel | ppm (wt.) | | 0.2 | 0.1 | 0.2 | 0.2 |
| D5708M (Vanadium) | Vanadium | ppm (wt.) | | 0.2 | 0.1 | 0.1 | 0.2 |

TABLE 1A-continued

| Analysis/Method | | | End user maximum allowed | Aggregate crude oil | Example 1 | Example 2 | Example 3 |
|---|---|---|---|---|---|---|---|
| D5708M (Silicon) | Silicon | ppm (wt.) | 4 | 1.9 | 2.1 | 1.8 | |
| D5708M (Iron) | Iron | ppm (wt.) | | 0.1 | 2 | 2.6 | 1.5 |
| D5708M (Copper) | Copper | ppm (wt.) | | 0.2 | 0.4 | 0.3 | 0.1 |
| D5708M (Zinc) | Zinc | ppm (wt.) | | 0 | 0 | 0 | 0 |
| Total Metals | | | 24 | 29.9 | 7.4 | 7.5 | 6.1 |
| | | Metal removal: | | | 75.25% | 74.92% | 79.60% |
| | | P removal: | | | 88.68% | 89.62% | 90.57% |

TABLE 1B

| Analysis/Method | | | Example 4 | Example 5 | Example 6 | Example 7 | Example 8 |
|---|---|---|---|---|---|---|---|
| D2709 | Total S&W | vol. % | <0.010 | <0.010 | <0.010 | <0.010 | <0.010 |
| D7536, Chloride In Hydrocarbons By XRF | Total Chloride | mg/kg | 3.09 | 2.83 | 2.91 | 3.6 | 2.86 |
| | | CL Removal: | 71.34% | 73.75% | 73.01% | 66.60% | 73.47% |
| Free Fatty Acids | Free Fatty Acids (calc) | % | 12.5 | 12.7 | 12.4 | 12.5 | 12.5 |
| D5708M (Calcium) | Calcium | ppm (wt.) | 0.8 | 0.6 | 0.5 | 0.1 | 0.1 |
| D5708M (Magnesium) | Magnesium | ppm (wt.) | 0.1 | 0.1 | 0.1 | 0.1 | 0.1 |
| D5708M (Sodium) | Sodium | ppm (wt.) | 1 | 0 | 0.7 | 0.2 | 0.3 |
| D5708M (Potassium) | Potassium | ppm (wt.) | 0.6 | 0.3 | 0.2 | 0 | 0.5 |
| D5708M (Phosphorous) | Phosphorus | ppm (wt.) | 1.2 | 1.8 | 1.3 | 1.6 | 0.9 |
| D5708M (Nickel) | Nickel | ppm (wt.) | 0 | 0.1 | 0.2 | 0.1 | 0.2 |
| D5708M (Vanadium) | Vanadium | ppm (wt.) | 0.2 | 0.2 | 0.2 | 0.2 | 0 |
| D5708M (Silicon) | Silicon | ppm (wt.) | 1.9 | 1.7 | 1.5 | 1.4 | 1.9 |
| D5708M (Iron) | Iron | ppm (wt.) | 1.2 | 1 | 1 | 1 | 1 |
| D5708M (Copper) | Copper | ppm (wt.) | 0.2 | 0.2 | 0.2 | 0.2 | 0.2 |
| D5708M (Zinc) | Zinc | ppm (wt.) | 0 | 0 | 0 | 0 | 0 |
| Total Metals | | | 7.2 | 6 | 5.9 | 4.9 | 5.2 |
| | | Metal removal: | 75.92% | 79.93% | 80.27% | 83.61% | 82.61% |
| | | P removal: | 88.68% | 83.02% | 87.74% | 84.91% | 91.51% |

TABLE 1C

| Analysis/Method | | | Example 9 | Example 10 | Example 11 |
|---|---|---|---|---|---|
| D2709 | Total S&W | vol. % | <0.010 | <0.010 | 0.015 |
| D7536, Chloride In Hydrocarbons By XRF | Total Chloride | mg/kg | 2.97 | 2.9 | 3.08 |
| | | CL Removal: | 72.45% | 73.10% | 71.43% |
| Free Fatty Acids | Free Fatty Acids (calc) | % | 12.3 | 12.5 | 12.2 |

TABLE 1C-continued

| Analysis/Method | | | Example 9 | Example 10 | Example 11 |
|---|---|---|---|---|---|
| D5708M (Calcium) | Calcium | ppm (wt.) | 0.1 | 0.1 | 0.1 |
| D5708M (Magnesium) | Magnesium | ppm (wt.) | 0.1 | 0.1 | 0.1 |
| D5708M (Sodium) | Sodium | ppm (wt.) | 0 | 0 | 0.1 |
| D5708M (Potassium) | Potassium | ppm (wt.) | 0.6 | 0.6 | 0.8 |
| D5708M (Phosphorous) | Phosphorus | ppm (wt.) | 1 | 1.8 | 1.7 |
| D5708M (Nickel) | Nickel | ppm (wt.) | 0.1 | 0.1 | 0.3 |
| D5708M (Vanadium) | Vanadium | ppm (wt.) | 0.2 | 0.2 | 0.2 |
| D5708M (Silicon) | Silicon | ppm (wt.) | 2.1 | 1.9 | 2.2 |
| D5708M (Iron) | Iron | ppm (wt.) | 0.6 | 0.5 | 0.3 |
| D5708M (Copper) | Copper | ppm (wt.) | 0.2 | 0.2 | 0.2 |
| D5708M (Zinc) | Zinc | ppm (wt.) | 0 | 0 | 0.1 |
| Total Metals | | | 5 | 5.5 | 6.1 |
| | | Metal removal: | 83.28% | 81.61% | 79.60% |
| | | P removal: | 90.57% | 83.02% | 83.96% |

Example 2

Extraction efficiency was measured for a single wash stage using a fiber reactor contactor device as in Example 1 with water as the sole extracting chemical in which crude DCO was the oil being pretreated. In these examples, DCO processed at an ethanol plant is purified using single wash step or single washing pass with water as the only washing ingredient. The DCO was processed in a continuous fashion at 15 GPM (gallons per minute) and the process resulted in 95% removal of total starting metal contaminants, as summarized in Table 2 below.

TABLE 2

| Metal Contaminants (ppm) | Crude DCO | Pure DCO | Removal |
|---|---|---|---|
| Calcium | 4.4 | 0.1 | 98% |
| Magnesium | 41.8 | 0.8 | 98% |
| Sodium | 52.6 | 3 | 94% |
| Potassium | 166.2 | 7.6 | 95% |
| Phosphorus | 128.4 | 13.8 | 89% |
| Nickel | 0.5 | 0.4 | 20% |
| Vanadium | 0.1 | 0.1 | 0% |
| Silicon | 74.6 | 5.7 | 92% |
| Copper | 0 | 0 | 0% |
| Zinc | 1.3 | 0.8 | 38% |
| Iron | 1.2 | 0.3 | 75% |
| Total Metals | 471.1 | 32.6 | 93% |
| Water & Sediment | 4.5 | 2.5 | 44% |

Example 3

The purification process used in Examples 1 and 2 was utilized in six ethanol plants to remove impurities from crude DCO. The results are shown in Table 3 below.

TABLE 3

| Metal Contaminants (ppm) | PLANT 1 Crude DCO | PLANT 1 Pure DCO | PLANT 2 Crude DCO | PLANT 2 Pure DCO | PLANT 3 Crude DCO | PLANT 3 Pure DCO | PLANT 4 Crude DCO | PLANT 4 Pure DCO | PLANT 5 Crude DCO | PLANT 5 Pure DCO | PLANT 6 Crude DCO | PLANT 6 Pure DCO |
|---|---|---|---|---|---|---|---|---|---|---|---|---|
| Calcium | 0.1 | 0 | 0 | 0 | 0 | 0 | 0.1 | 0 | 0 | 0 | 0.2 | 0 |
| Magnesium | 2.2 | 0 | 1 | 0.1 | 2.2 | 0.1 | 1.5 | 0 | 1.7 | 0.1 | 2.8 | 0 |
| Sodium | 1.8 | 1.1 | 18.2 | 1.6 | 9.3 | 3.1 | 2.5 | 0.2 | 2.3 | 0.3 | 5.5 | 0.6 |
| Potassium | 25.3 | 0 | 9.3 | 0 | 10.9 | 0 | 15.4 | 1.1 | 8.9 | 0.8 | 17.1 | 0.6 |
| Phosphorus | 22.2 | 3.4 | 9.9 | 3.6 | 13.8 | 6 | 14.7 | 3.5 | 9.9 | 3.5 | 8.7 | 2.4 |
| Iron | 0.9 | 0.5 | 0.1 | 0.1 | 0.2 | 1.4 | 0.9 | 1.4 | 1.1 | 0.5 | 7.2 | 0.1 |
| Zinc | 1.1 | 0.2 | 0.3 | 0.3 | 1.1 | 0.5 | 0.4 | 0.4 | 0.5 | 0.3 | 1.8 | 0.2 |
| Nickel | 0.1 | 0.4 | 0.1 | 0.3 | 0.2 | 0.3 | 0.1 | 0.3 | 0.2 | 0.1 | 0.1 | 0.1 |
| Vanadium | 0 | 0 | 0 | 0 | 0 | 0 | 0 | 0 | 0 | 0 | 0 | 0 |
| Silicon | 38.9 | 3.5 | 18.6 | 7.5 | 5.7 | 1.3 | 24.2 | 4.2 | 46.1 | 6.1 | 15.6 | 2.2 |
| Cooper | 0 | 0 | 0 | 0 | 0 | 0 | 0 | 0 | 0 | 0 | 0 | 0 |
| Total Metals | 92.6 | 9.1 | 57.5 | 13.5 | 43.4 | 12.7 | 59.8 | 11.1 | 70.7 | 11.7 | 59 | 6.2 |
| % Removal | | 90% | | 77% | | 71% | | 81% | | 83% | | 89% |

Example 4

Removal of inorganic chlorides was measured for the purification process described in Example 3. The results are summarized in Table 4 below.

TABLE 4

| Ethanol | Inorganic Chlorides, ppm | | |
|---|---|---|---|
| Plant | Crude DCO | Pure DCO | % Removal |
| Plant 1 | 1.6 | 0.2 | 88% |
| Plant 2 | 1 | 0.2 | 80% |
| Plant 3 | 2.3 | 0.2 | 91% |
| Plant 4 | 2 | 0.2 | 90% |
| Plant 5 | 1.4 | 0.2 | 86% |
| Plant 6 | 2.1 | 0.2 | 90% |

Example 5

Samples of crude DCO were purified using the process described in Example 1. The amount of FFA before and after purification were measured and the results are summarized in Table 5 below.

TABLE 5

| Sample | % FFA in Crude | % FFA in Pure | Δ |
|---|---|---|---|
| 1 | 13.70 | 13.20 | 0.50 |
| 2 | 11.49 | 11.20 | 0.29 |
| 3 | 9.99 | 9.50 | 0.49 |
| 4 | 13.33 | 13.79 | −0.46 |
| 5 | 13.48 | 13.47 | 0.01 |
| 6 | 14.05 | 14.32 | −0.27 |
| 7 | 13.97 | 14.26 | −0.29 |
| 8 | 13.99 | 13.95 | 0.04 |
| 9 | 13.99 | 13.95 | 0.04 |
| 10 | 14.19 | 14.26 | −0.07 |
| 11 | 14.48 | 14.56 | −0.08 |
| 12 | 9.73 | 10.01 | −0.28 |
| 13 | 13.77 | 13.63 | 0.14 |
| 14 | 11.91 | 12.07 | −0.16 |
| σ | | | 0.29 |

Although the present disclosure has been described using preferred embodiments and optional features, modification and variation of the embodiments herein disclosed can be foreseen by those skilled in the art, and such modifications and variations are considered to be within the scope of the present disclosure. It is also to be understood that the above description is intended to be illustrative and not restrictive. Many alternative embodiments will be apparent to those of in the art upon reviewing the above description. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the disclosure.

What is claimed is:

1. A method for co-production of ethanol and pretreatment of a diesel feedstock, comprising:
   distilling an ethanol-containing beer within a distillation apparatus of an ethanol plant using grain as a feedstock;
   producing ethanol and a crude vegetable oil product in the ethanol plant;
   directing the crude vegetable oil product from the ethanol plant to a pretreatment plant comprising a fiber reactor comprising a conduit having a plurality of fibers disposed therein;
   in the pretreatment plant, purifying the crude vegetable oil product by contacting the crude vegetable oil product with an aqueous extractant solution within the fiber reactor to produce a purified oil and wastewater, wherein the aqueous extractant solution consists of water or purified water; and
   recycling the wastewater from the pretreatment plant to the ethanol plant;
   wherein purifying the crude vegetable oil removes 70% or more of impurities.

2. The method of claim 1, wherein the impurities comprise renewable diesel catalyst poisons.

3. The method of claim 1, wherein the wastewater comprises minerals, metals, and/or phospholipids and the method further comprises enriching a coproduced product of the ethanol plant with the minerals, metals, and/or phospholipids.

4. The method of claim 1, recycling the wastewater comprises utilizing the wastewater as cook water in the ethanol plant.

5. The method of claim 1, wherein recycling the wastewater comprises incorporating the wastewater into a mash bill in the ethanol plant.

6. The method of claim 1, wherein the pretreatment plant uses low shear transfer and mixing to minimize emulsion formation.

7. The method of claim 1, wherein a second crude vegetable oil from off-site production is processed in the pretreatment plant.

8. A method for co-production of ethanol and pretreatment of a diesel feedstock, comprising:
   preparing a starch rich mash for fermentation;
   fermenting the mash into an ethanol-containing beer;
   distilling the ethanol-containing beer within a distillation apparatus of an ethanol plant, thereby producing a crude oil comprising vegetable oil, fat, wax rich material, or combinations thereof;
   directing the crude oil to a pretreatment plant;
   in the pretreatment plant, purifying the crude oil with an aqueous extractant solution to produce a purified and wastewater, wherein the aqueous extractant solution consists of water or purified water; and
   recycling the wastewater from the pretreatment plant to the ethanol plant;
   wherein purifying the crude oil removes 70% or more of impurities.

9. The method of claim 8, wherein the impurities comprise renewable diesel catalyst poisons.

10. The method of claim 8, wherein the pretreatment plant uses low shear transfer and mixing to minimize emulsion formation.

11. The method of claim 8, wherein the pretreatment plant uses a fiber reactor to facilitate mixing and mass transfer between the oil phase and the water phase, the fiber reactor comprising a conduit having a plurality of fibers disposed therein.

12. The method of claim 8, wherein a second crude oil from off-site production is processed in the pretreatment plant.

13. A system for co-production of ethanol and pretreatment of a diesel feedstock, comprising:
an ethanol plant comprising;
one or more fermentation tanks configured to ferment a starch rich mash into an ethanol-containing beer; and
a distillation apparatus configured to distill the ethanol-containing beer;
wherein the ethanol plant produces a crude oil; and
a pretreatment plant comprising:
a water supply, the water supply containing an aqueous treatment solution consisting of water or purified water; and
a pretreatment tank comprising:
a first inlet connected to the ethanol plant and configured to receive the crude oil from the ethanol plant;
a second inlet connect to the water supply and configured to receive the aqueous treatment solution;
a first outlet configured to remove a purified oil from the pretreatment tank; and
a second outlet configured to direct wastewater from the pretreatment plant to the ethanol plant.

14. The system of claim 13, wherein the second outlet is connected via a line to a cook water tank within the ethanol plant.

15. The system of claim 13, wherein the second outlet is connected via a line to a vessel within the ethanol plant containing a mash bill.

16. The system of claim 13, wherein the pretreatment plant uses low shear transfer and mixing to minimize emulsion formation.

17. The system of claim 13, wherein the pretreatment plant uses a fiber reactor to facilitate mixing and mass transfer between the oil phase and the water phase, the fiber reactor comprising a conduit having a plurality of fibers disposed therein.

18. The system of claim 13, wherein a second crude oil from off-site production is processed in the pretreatment plant.

* * * * *